(12) United States Patent
Fleche et al.

(10) Patent No.: US 6,300,494 B1
(45) Date of Patent: Oct. 9, 2001

(54) PROCESS FOR THE MANUFACTURE OF D-ERYTHROSE

(75) Inventors: Guy Fleche, Hazebrouck; Rodolphe Tamion, Allouagne, both of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 08/926,010

(22) Filed: Sep. 9, 1997

(30) Foreign Application Priority Data

Sep. 16, 1996 (FR) .................................................. 96 11255

(51) Int. Cl.[7] ...................................................... C07H 1/00
(52) U.S. Cl. ........................................... 536/124; 536/18.5
(58) Field of Search ..................................... 536/124, 18.5

(56) References Cited

U.S. PATENT DOCUMENTS

| | | | |
|---|---|---|---|
| 2,986,495 | 5/1961 | Onishi | 195/37 |
| 3,755,294 | 8/1973 | Walon | 260/209 |
| 3,756,917 | 9/1973 | Dezeeuw et al. | 195/28 |
| 4,845,208 | 7/1989 | Fuertes et al. | 536/124 |

FOREIGN PATENT DOCUMENTS 0 716 067   6/1996  (EP).

OTHER PUBLICATIONS

Perlin A.S.—Methods Carbohydr. Chem. 1, 1962, pp. 61–63.
Schaffer R.—J. Am. Chem. Soc. 81 (1959), 2838.
Barker R & MacDonald D.L., J. Amer Chem. Soc. 82 (1960), 2301.
Dooms, L. & al / Antonie Van Leeuwenhoek 37, (1971) p 107–118.
Hockett R.C. & Hudson C.S. / J. Amer. Chem. Soc. 56, (1934) p 1632–1633.
Fletcher H.G. & Hudson C.S./J. Amer. Chem. Soc. 72, (1950) p 4546.

*Primary Examiner*—James O. Wilson
*Assistant Examiner*—Howard V. Owens
(74) *Attorney, Agent, or Firm*—Henderson & Sturm LLP

(57) ABSTRACT

The invention relates to a process for the manufacture of D-erythrose, characterized in that an aqueous solution of a salt of gluconic acid is brought into contact with hydrogen peroxide in the presence of a salt of a metal selected from the group consisting of cobalt, nickel and ruthenium. It also relates to a process for the manufacture of erythritol by hydrogenation of D-erythrose thus obtained.

11 Claims, No Drawings

PROCESS FOR THE MANUFACTURE OF D-ERYTHROSE

The subject of the present invention is a process for the manufacture of D-erythrose.

More specifically, the subject of the present invention is a process for the manufacture of D-erythrose from gluconic acid, which process is catalysed by ions of a metal selected from the group consisting of cobalt, nickel and ruthenium and takes place in the aqueous phase.

Processes for the manufacture of D-erythrose are already known.

Among these, mention may firstly be made of that developed by Ruff (Ber., 32, 3674 (1899); 33, 1799 (1900)), which consists in oxidizing calcium D-arabinonate in the presence of aqueous hydrogen peroxide solution. Such a process exhibits the major disadvantage of using arabinonic acid, which is not a common commercially available product, as starting material.

Other processes for the manufacture of D-erythrose have followed, such as the oxidation of D-glucose in the presence of lead tetraacetate, known under the name of the Perlin method (Perlin A. S., Methods Carbohydr. Chem., 1962, 1, 64), or the acid hydrolysis of 2,4-O-ethylidene-D-erythrose obtained by the oxidation with periodate of 4,6-O-ethylidene-D-glucose (Schaffer R., J. Am. Chem. Soc., 81 (1959), 2838; Barker R. and MacDonald D. L., J. A. Chem. Soc., 82 (1960), 2301).

D-Erythrose is not of great interest in itself but would be in particular a very important synthetic intermediate if it came to pass that it could be produced on a large scale and at a low cost.

This is because a simple additional stage of hydrogenation of D-erythrose makes it possible easily to obtain erythritol, which is a polyol which can be employed in many food applications and in particular as non-cariogenic and low-calorie substitute for sucrose.

For this reason, another subject of the present invention is a process for the manufacture of erythritol starting from D-erythrose obtained in accordance with the process of the invention.

Although widespread in nature and having formed part of the human diet from time immemorial, erythritol has for a long time been ignored by the food industry, because of the difficulties encountered in obtaining it in a financially viable way.

In the pharmaceutical industry, erythritol can be oxidized to L-erythrulose, a molecule which has an advantageous functionality conferring on it the possibility of being used in the synthesis of biologically active compounds.

Studies which have been carried out on processes for the manufacture of erythritol have, taken as a whole, been divided into two main routes: chemical synthesis and fermentative biosynthesis.

None of the known chemical synthesis techniques, such as reduction of meso-tartrate, oxidation/reduction of 4,6-O-ethylidene-D-glucose and hydrogenation of starch dialdehyde hydrolysates (T. Dola and T. Sasaki, Bio-Industry, (1988), 5, (9), 32), has been able, however, to achieve a true industrial dimension.

Although markedly more numerous than in chemical synthesis, studies carried out on fermentation techniques are in the great majority of cases concerned with the production of erythritol as a secondary constituent.

These studies have been devoted to the production of erythritol by the yeasts Debaryomyces (U.S. Pat. No. 2,986,495), Pichia (U.S. Pat. No. 2,986,495), Candida (U.S. Pat. No. 3,756,917), Moniliella (Antonie van Leeuwenhoek, 37 (1971), 107–118), and Aureobasidium (JP-A 61/31,091).

The results provided to date by studies on the fermentation of erythritol nevertheless bring out a certain number of disadvantages, such as foaming during fermentation, the rate of fermentation, the extent of the byproducts and especially the poor yield, which further jeopardise the possibilities of the industrialization thereof.

There thus existed a need to develop a high-performance process for the manufacture of D-erythrose (and thus of erythritol by hydrogenation of the D-erythrose thus obtained) which does not exhibit the limitations and/or the disadvantages of the prior art.

It was while working on this research theme that the Applicant Company developed a new process for the manufacture of D-erythrose by the chemical route from gluconic acid or its salts. The process in accordance with the invention goes back to the principle of the method described by Ruff nearly a century ago.

This method makes it possible, in a general way, to convert an aldonic acid containing n carbons to an aldose containing (n-1) carbons, by virtue of the combined action of ferric ions and of aqueous hydrogen peroxide solution. However, the aldose yields are very modest.

Thus, the conversion of gluconic acid to D-arabinose is carried out according to this method.

A few improvements have subsequently been introduced by R. C. Hockett and C. S. Hudson (J. Amer. Chem. Soc., 56, 1632–1633, (1934) and ibid., 72, 4546, (1950)) and by the document U.S. Pat. No. 3,755,294. Arabinose yields of 60%, starting from gluconic acid, are described therein. Progress has been accomplished by V. Bilik (CZ-232647, (1983)) by using cupric (Cu(II)) ions as catalysts. Yields of the order of 70% are achieved after a laborious purification.

Identical results were recently obtained with a mixture of ferric and ferrous ions as catalysts (CZ-279002, (1994)).

Finally, under specific conditions, the document EP-A 0,716,067 reports yields of certain aldoses of 78%.

During a widescale investigation of the Ruff reaction, the Applicant Company has discovered that cobalt, nickel and ruthenium salts catalysed the reaction of gluconic acid with aqueous hydrogen peroxide solution to give, surprisingly, D-erythrose and not, as might have been expected, D-arabinose. Two carbon atoms are thus lost with respect to the starting aldonic acid.

Thus, according to the invention, the process for the manufacture of D-erythrose is characterized in that an aqueous solution of a salt of gluconic acid is brought into contact with hydrogen peroxide in the presence of a salt of a metal selected from the group consisting of cobalt, nickel and ruthenium.

A first advantage in such a process, in comparison with the fermentation processes of the prior art, is obviously that it avoids all the restrictions and problems related to the fermentation techniques as mentioned above.

A second advantage of the process in accordance with the invention lies in the fact that it is extremely easy to implement since both the starting material and the reagents are readily accessible.

A third advantage of the process in accordance with the invention is that D-erythrose is obtained with a very good yield close to stoichiometric.

Another advantage of the process in accordance with the invention is that it readily finds a place in industry, in particular the food industry, because it uses water as solvent, which is an undeniable advantage both as regards toxicity and as regards safety.

The process of the invention makes use of a salt of gluconic acid.

In the present invention, salt of gluconic acid is understood to mean gluconic acid in the free form, in the lactone form or in the form of a mixture of these two forms, in the form of salts or in the form of esters. Thus, for example, calcium gluconate, sodium gluconate or δ-gluconolactone are entirely suitable.

Gluconic acid is obtained in a known way by oxidation of glucose. This oxidation stage can be carried out either by the chemical route or by the microbiological route.

The preferred chemical route in the context of the invention consists in oxidizing glucose using air or oxygen in alkaline medium and using palladium catalysts.

A particularly preferred process is that which has been described in United States Patent U.S. Pat. No. 4,845,208, of which the Applicant Company is an assignee, which consists in using, as oxidation catalyst, palladium attached to active charcoal and doped with bismuth.

It is also possible to envisage the oxidation of glucose by the electrolytic route or using hypobromite. It is also possible to oxidize glucose by the microbiological route using Gluconobacter or Aspergillus.

The process of the invention is preferably implemented, in water, with a content of salt of gluconic acid, as dry matter, of between 1 and 60%, preferentially between 5 and 50% and more particularly between 10 and 30%.

The lower dry matter constraints are imposed for obvious reasons of economy in evaporating water and in reducing the size of the reactors.

The upper dry matter constraints are essentially imposed by problems of solubility or of viscosity of the reaction mixture.

In the present description, all the percentages are expressed with respect to gluconic acid (example: 50 mol % means 50 mol of X per 100 mol of gluconic acid and 50% means 50 g of X per 100 g of starting gluconic acid).

In the process in accordance with the invention, the catalyst is composed of ions of a metal selected from the group consisting of cobalt, nickel and ruthenium, which ions can be introduced in the form of any divalent or trivalent cobalt, nickel or ruthenium salt. Preference is advantageously given to cobalt salts: cobalt acetate, acetylacetonate, halides, nitrate, sulphate, and the like, for example, are entirely suitable.

An amount of catalyst (cobalt, nickel or ruthenium salt) of between 0.001 and 50%, preferentially between 0.002 and 20% and more particularly between 0.005 and 5%, with respect to the salt of gluconic acid employed, gives good results in the process in accordance with the invention, both as regards the yield and the purity of the D-erythrose obtained.

Hydrogen peroxide, preferably in the form of an aqueous hydrogen peroxide solution with a concentration of 30%, is then slowly added with stirring to the mixture of salt of gluconic acid, of catalyst and of water thus produced, the hydrogen peroxide being in a proportion of 1 to 500 mol %, preferentially of 50 to 400 mol % and more particularly of 100 to 300 mol %, with respect to the salt of gluconic acid employed.

It is possible to use hydrogen peroxide in the form of an aqueous hydrogen peroxide solution with a concentration greater than 30%, in particular, for example, up to 70%.

The aqueous hydrogen peroxide solution is added at a rate of introduction such that the temperature of the reaction mixture does not rise, preferably, beyond 50° C. and more particularly beyond 35° C. Thus, the rate of introduction of the aqueous hydrogen peroxide solution generally lies between 30 minutes and 2 hours.

The process of the invention is preferably implemented at a temperature of between 0 and 100° C. and preferentially between 10 and 50° C.

Lower temperatures result in excessively long reaction times and higher temperatures, apart from the fact that they would require the use of pressure-resistant reactors, would result in degradation of the reaction products.

Temperatures of 20 to 40° C. are thus particularly preferred in the process of the invention.

Preferably again, the process of the invention is implemented at a pH of between 2 and 12, preferentially of between 5 and 8 and more particularly of between 6 and 7.

The D-erythrose obtained in accordance with the process of the invention, in its crude form, can then easily be catalytically hydrogenated.

The hydrogenation of such a sugar is carried out in accordance with the rules of the art, which result, for example, in the production of sorbitol from glucose.

Both ruthenium-based catalysts and Raney nickel catalysts can be used for this stage.

However, it is preferable to use Raney nickel catalysts, which are less expensive.

In practice, from 1 to 10% by weight of catalyst is used with respect to the sugar, as dry matter, subjected to the hydrogenation. The hydrogenation is preferably carried out on syrups with a dry matter content of between 15 and 50%, in practice in the region of 30 to 45%, under a hydrogen pressure of between 20 and 200 bars. It can be carried out continuously or batchwise.

When batchwise hydrogenation is carried out, the hydrogen pressure used is generally between 30 and 60 bars and the temperature at which the hydrogenation is carried out is between 100 and 150° C. Care is also taken to maintain the pH of the hydrogenation mixture by the addition of sodium hydroxide or of sodium carbonate, for example, but without exceeding a pH of 9.0. This way of carrying out the hydrogenation makes it possible to prevent the appearance of cracking or isomerization products.

The reaction is halted when the content of reducing sugars in the reaction mixture has become less than 1%, more preferably less than 0.5% and more particularly less than 0.1%.

After cooling the reaction mixture, the catalyst is removed by filtration and the D-erythritol thus obtained is demineralized through cationic and anionic resins.

At this stage, the syrups contain at least 90% of D-erythritol and it is easy to purify the latter therefrom by crystallization after concentrating and cooling the solutions.

The invention will be better understood by means of the following examples, the sole aim of which is to better illustrate the invention without desiring to reduce it to the embodiments expressly described and to the sole gluconate, of calcium, employed.

In the following examples, all the results are expressed as molar percentages.

EXAMPLE 1

Calcium gluconate monohydrate (115.7 g, 0.255 mol), cobalt chloride hexahydrate (0.58 g, 2.4 mmol) and water (1000 ml) are introduced into a jacketed reactor.

The mixture is brought to a temperature of 30° C. and to a pH of 6.5 by addition of 2N sodium hydroxide solution.

Aqueous hydrogen peroxide solution (130 ml, 1.28 mol) is introduced over 70 minutes while maintaining the temperature between 30 and 35° C. and the pH at 6.5 using 2N sodium hydroxide solution.

At the end of the addition, the solution is stirred for a further one hour. The pH is brought to between 2.5 and 3 by addition of concentrated sulphuric acid (14 ml), in order to precipitate the calcium salts.

After filtration, the pink solution has the following composition: D-erythrose (87%), D-arabinose (2%) and gluconic acid (7%).

The percentages given are those corresponding to the analytical results. The sum is not equal to 100 because there is sometimes formation of a small amount of arabinonic acid (2%) and of other byproducts.

These byproducts are: formic acid, "carbonates" and carbon dioxide.

Example 2

Calcium gluconate monohydrate (115.1 g, 0.25 mol), nickel chloride hexahydrate (2.24 g, 9.5 mmol) and water (1000 ml) are introduced into a jacketed reactor. The mixture is brought to a temperature of 40° C. and to a pH of 6.5 by addition of 2 N sodium hydroxide solution. 35% aqueous hydrogen peroxide solution (95 ml, 1.1 mol) is introduced over 70 minutes while maintaining the temperature between 40 and 45° C. and the pH at 6.5 using 2N sodium hydroxide solution. At the end of the addition, the solution is stirred for a further 3 hours. The pH is brought to 2.5 by addition of concentrated sulphuric acid (14 ml), in order to precipitate the calcium salts. After filtration, the green solution has the following composition: D-erythrose (40%) and gluconic acid (45%).

The percentages given are those corresponding to the analytical results. The sum is not equal to 100 because there is also formation of glyceraldehyde (6%) and of arabinose (2%).

The reaction byproducts are: formic acid and carbon dioxide.

What is claimed is:

1. A process, comprising the step of:
   bringing an aqueous solution of a salt of gluconic acid into contact with hydrogen peroxide in the presence of a salt of a metal selected from the group consisting of cobalt, nickel and ruthenium to produce D-erythrose.

2. Process according to claim 1, wherein the aqueous solution has a content of salt of gluconic acid, as dry matter, of between 1 and 60%.

3. Process according to claim 1, wherein the salt of a metal selected from the group consisting of cobalt, nickel and ruthenium is present in an amount of between 0.001 and 50%, expressed with respect to the salt of gluconic acid.

4. Process according to claim 1, wherein hydrogen peroxide is used in the form of an aqueous hydrogen peroxide solution with a concentration of 30%, in an amount of between 1 and 500 mol %, expressed with respect to the salt of the gluconic acid.

5. Process according to claim 1, wherein the reaction is carried out at a temperature of between 0 and 100° C.

6. Process according to claim 5, wherein the reaction is carried out at a temperature of between 10 and 50° C.

7. Process according to claim 1, wherein the reaction is carried out at a pH of between 2 and 12.

8. Process according to claim 7, wherein the reaction is carried out at a pH of between 5 and 8.

9. Process according to claim 1, wherein the salt of gluconic acid is obtained by oxidation of glucose carried out using air or oxygen, in alkaline medium, in the presence of palladium catalysts.

10. Process according to claim 1, wherein the salt of gluconic acid is obtained by oxidation of glucose via the microbiological route.

11. The process of anyone of claims 1–10, further comprising the step of hydrogenating said D-erythrose to produce erythritol.

* * * * *